United States Patent [19]

Larsen et al.

[11] Patent Number: 4,924,860

[45] Date of Patent: May 15, 1990

[54] WATER TRAP AND ASSOCIATED CONTROL SYSTEM

[75] Inventors: Timothy P. Larsen, Wauwatosa; James A. Devine, Waukesha; Michael T. Larsen, Wauwatosa, all of Wis.

[73] Assignee: Criticare Systems, Inc., Waukesha, Wis.

[21] Appl. No.: 237,136

[22] Filed: Aug. 26, 1988

[51] Int. Cl.[5] .............................. A62B 7/00; A61B 5/08
[52] U.S. Cl. ...................... 128/205.12; 128/204.21; 128/719
[58] Field of Search ............. 55/528; 128/205.12, 128/719, 204.21

[56] References Cited

U.S. PATENT DOCUMENTS

| | | | |
|---|---|---|---|
| 4,197,858 | 4/1980 | Osborn | 128/718 |
| 4,293,378 | 10/1981 | Klein | 55/528 |
| 4,327,718 | 5/1982 | Cronenberg | 128/205.12 |
| 4,417,574 | 11/1983 | Talonn et al. | 128/205.12 |
| 4,445,012 | 4/1984 | Blackburn et al. | 200/61.04 |
| 4,446,869 | 5/1984 | Knodle | 128/719 |
| 4,549,553 | 10/1985 | Hochberg | 128/205.12 |
| 4,558,708 | 12/1985 | Labuda et al. | 128/719 |
| 4,575,385 | 3/1986 | Brooks et al. | 55/528 |
| 4,579,568 | 4/1986 | Ricciardelli et al. | 155/189 |
| 4,592,368 | 6/1986 | Ricciardelli et al. | 128/719 |
| 4,668,258 | 5/1987 | Steer | 55/528 |
| 4,713,095 | 12/1987 | Ricciardelli | 55/189 |

*Primary Examiner*—Edgar S. Burr
*Assistant Examiner*—Kimberly L. Asher
*Attorney, Agent, or Firm*—Willian Brinks Olds Hofer Gilson & Lione

[57] ABSTRACT

A water trap for a gas analyzer includes self-sealing filters formed of a porous polymer that includes a cellulose extract that causes the polymer to become impermeable on contact with water. The water trap in this way automatically protects the gas analyzer from liquid contamination. Preferably, the gas analyzer monitors a pressure parameter of a pneumatic line connected to the water trap and provides an indication that the water trap should be replaced in the event this pressure parameter indicates an abnormal operating condition.

16 Claims, 3 Drawing Sheets

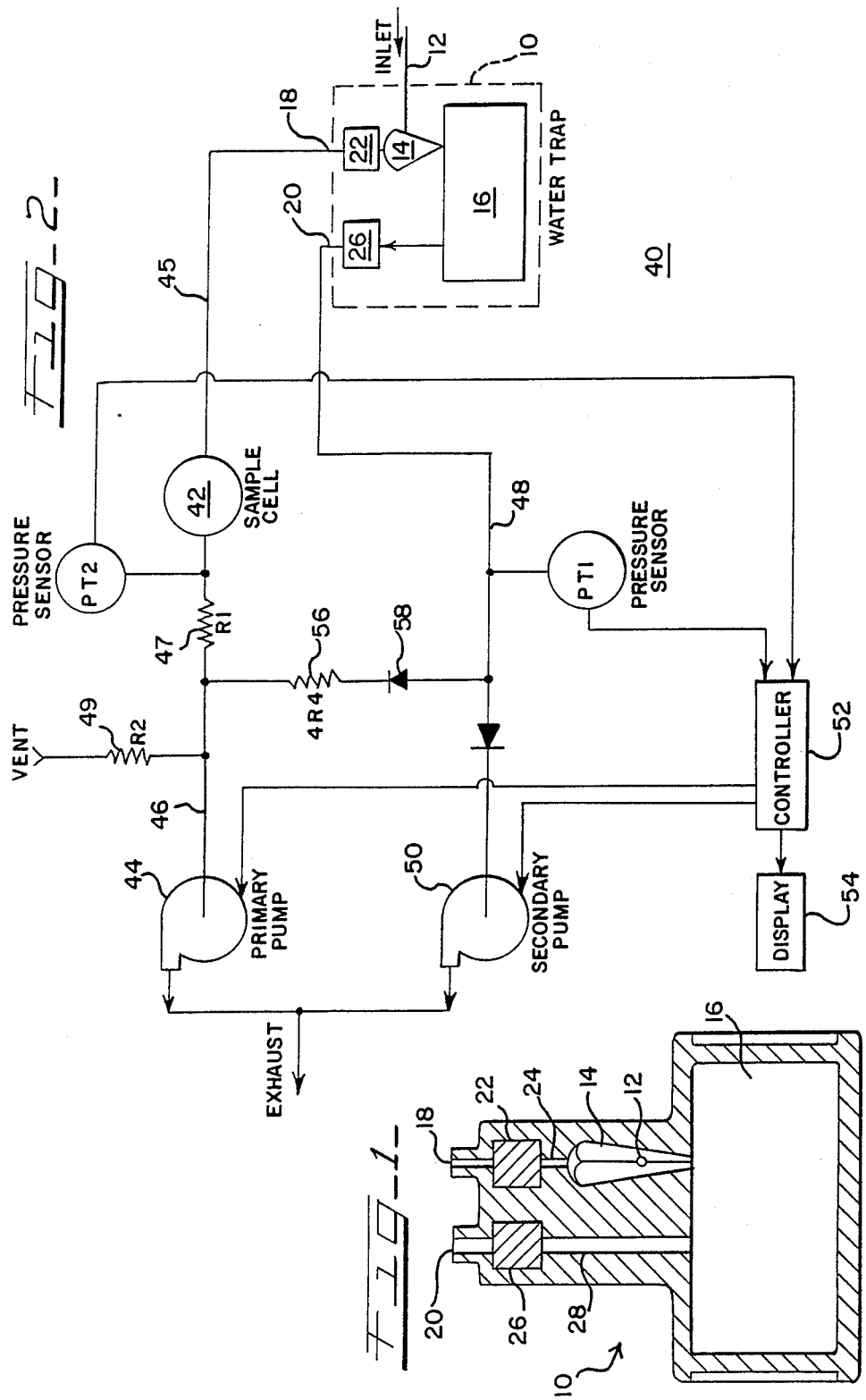

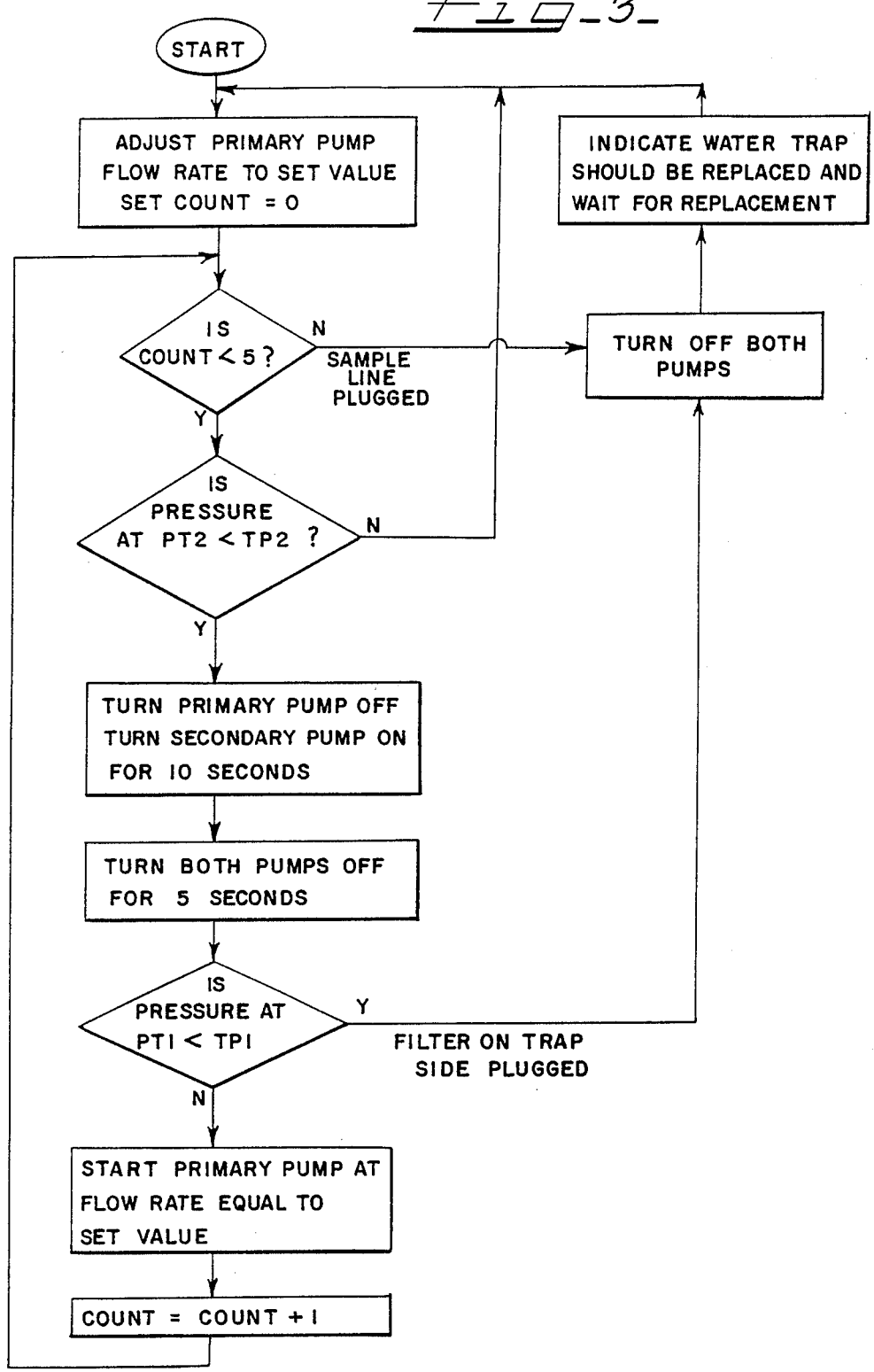

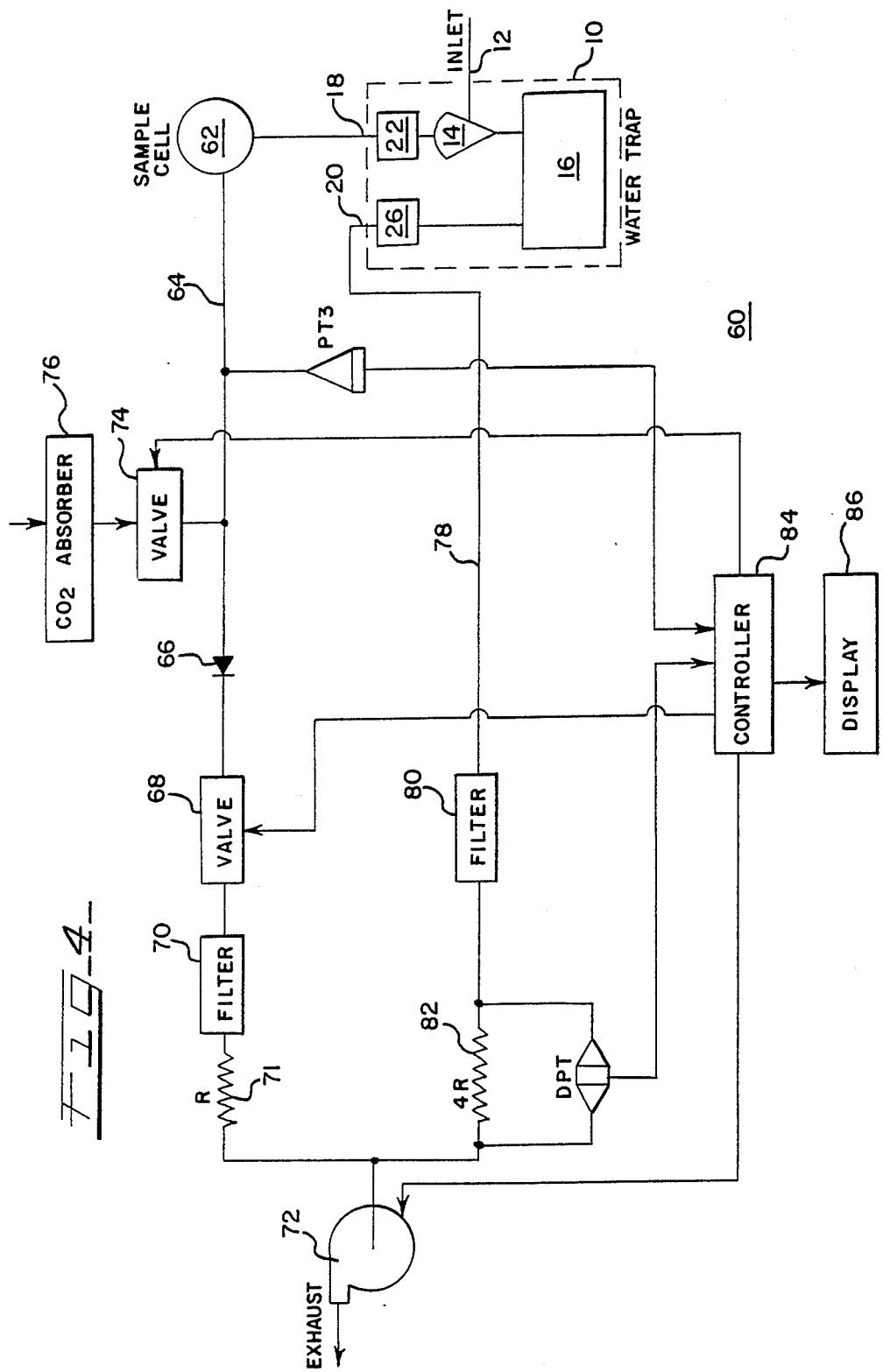

WATER TRAP AND ASSOCIATED CONTROL SYSTEM

BACKGROUND OF THE INVENTION

This invention relates to an improved water trap for a respiratory gas analyzer, and to an improved control system for use with such a water trap.

Respiratory gas analyzers monitor exhaled air from a patient, and it has longed been recognized that means must be provided for removing excess moisture from the exhaled air prior to analysis. Ricciardelli U.S. Pat. No. 4,579,568, and U.S. Pat. No. 4,713,095 (the latter assigned to the assignee of the present invention) both disclose water traps for use with respiratory gas analyzers.

Such water traps can become filled, and the sample inlet line that conducts exhaled air to the water trap can become blocked with condensed moisture. Ricciardelli U.S. Pat. No. 4,592,368 discloses one gas analyzer protection system which monitors pressure in a pneumatic line that passes through the sample cell of the gas analyzer to the water trap. In the event of excessively low pressures, indicative of a clogged line, the disclosed control system alters flow directions and rates so as to back flush selected lines to protect the gas analyzer. The water traps of the above-identified *Ricciardelli* patents fail to include any means for sealing lines of the system in the event the water trap becomes over filled and can no longer perform its water trap function.

Osborn U.S. Pat. No. 4,197,858 and Blackburn U.S. Pat. No. 4,445,012 both disclose moisture sensing systems used to protect a gas analyzer from water. In the Osborn system, water level in a water trap container 13 is sensed when water provides a conductive path between two electrodes 21, 23. When this conductive path is created, the presence of excess water in the container 13 is sensed and a valve is opened to back flush the system. In the Blackburn system, spaced electrodes are provided in a line and a system monitors the resistance between the electrodes in order to detect the presence of moisture in the line that bridges the gap between the electrodes. When water is sensed in the line a pump is activated to purge the line with injected gas.

Knodle U.S. Pat. No. 4,446,869 discloses a water absorbing trap to protect an infrared exhaled carbon dioxide apnea monitor. The water trap includes a water absorbing polymer 53 and a second polymer 68 having a passageway formed therethrough. When the second polymer 68 comes into contact with water that has passed through the first polymer 51, the second polymer swells and closes the passageway. In column 2, lines 10-22, reference is made to the fact that the apnea monitor indicates by sight and sound alarms the fact that the second polymer has swelled shut in the same way that such alarms are used when a patient stops breathing. The preferred diameter for the passageway in the the second polymer is 0.04 inches.

The present invention is directed to an improved water trap which positively seals the exit ports of the water trap in a high speed and reliable manner in the event water is passed out of the water trap.

In addition, this invention is directed to an improved control system that utilizes pressure sensors to detect sealing of a self-sealing filter in a water trap of the type described above in order to provide an indication of an abnormal condition.

SUMMARY OF INVENTION

According to this invention, a water trap is provided for a respiration gas analyzer. The water trap of this invention includes a tapered water separation chamber. A sample inlet port is connected to the water separation chamber, and gas samples are withdrawn from the separation chamber via a sample outlet port conduit. The water trap also includes a water collection chamber connected to receive water from the water separation chamber. A vacuum port is connected to the water collection chamber by a vacuum conduit, and at least one self-sealing filter is disposed in at least one of the sample outlet conduit in the vacuum conduit. This self-sealing filter comprises of porous matrix having a size less than about 500 microns and means, disposed in the porous matrix, for rendering the porous matrix substantially non-porous when exposed to water.

The self-sealing filter of this water trap provides high speed response to prevent substantially any water from leaving the water trap. Because it does not define any presized or prepositioned through passageways, it can be manufactured and installed at low cost.

According to another feature of this invention, a control system is provided for a gas analyzer of the type comprising a sample cell, a water trap comprising a separation chamber interconnected with a water collection chamber, a low pressure source, and a conduit system comprising a first conduit for conducting a sample gas from an inlet line to the separation chamber, a second conduit for conducting the sample gas from the separation chamber through the sample cell to the low pressure source, a third conduit for conducting a gas from the water collection chamber to the low pressure source. The control system of this invention includes means, included in the third conduit, for automatically sealing the third conduit upon contact with water. A pressure sensor is coupled to the third conduit to generate a pressure signal indicative of a pressure parameter of a selected portion of the third conduit. Means are provided, responsive to the pressure signal, for detecting values of the pressure signal indicative of an abnormally low flow through the third conduit. An indicating means indicates an abnormal condition when the detecting means detects abnormally low flow. Preferably, the water trap used in the control system of this invention is the water trap described above.

The control system of this invention provides the important advantage that it does not rely on water level sensing or water conductivity to recognize the abnormal condition. Rather, a pressure sensor is used in the conduit that conducts fluid from the water collection chamber to the low pressure source. This approach to detecting a sealed conduit is reliable, and is not subject to errors associated with changes in liquid conductivity, water droplet size, or splashing.

The invention itself, together with further objects and attendant advantages, will best be understood by reference to the following detailed description taken in conjunction with the accompanying drawings.

BRIEF DESCRIPTION OF DRAWINGS

FIG. 1 is a cross-sectional view of a preferred embodiment of the improved water trap of this invention.

FIG. 2 is a schematic view of a gas analyzer which includes a first preferred embodiment of the control system of this invention.

FIG. 3 is a flow chart detailing operation of the control system of FIG. 2.

FIG. 4 is a schematic representation of a gas analyzer which incorporates a second preferred embodiment of the control system of this invention.

DETAILED DESCRIPTION OF THE PRESENTLY PREFERRED EMBODIMENTS

Turning now to the drawings, FIG. 1 shows a water trap 10 which incorporates a presently preferred embodiment of this invention. This water trap 10 includes a water separation chamber 14 and a water collection chamber 16. Preferably the water separation chamber has a volume less than one milliliter. A sample respiration gas of exhaled air is introduced into the separation chamber 14 via a sample inlet port 12. Water from the sample exits the separation chamber 14 to the water collection chamber 16, while the sample leaves the separation chamber 14 via a sample outlet port 18. A vacuum port 20 is normally in fluid communication with the collection chamber 16 via a conduit 28. The sample outlet port 18 is normally in communication with the separation chamber 14 via a conduit 24. The foregoing features of the water trap 10 are described in much greater detail in U.S. Pat. No. 4,717,095, which is hereby incorporated by reference for its detailed teaching of the construction for the above-referenced elements of the water trap 10.

According to this invention, the water trap 10 includes two self-sealing filters 22, 26, each disposed in a respective one of the conduits 24, 28. Each of the self-sealing filters 22, 26 is formed of a porous plastic material which includes means for rendering the material non-porous upon exposure to water. The porous material included in the self-sealing filters 22, 26 should have a pore diameter of less than 100 microns, preferably less than 50 microns, and most preferably in the range of 15 to 35 microns. The means for sealing the filters 22, 26 in response to water contact is preferably a cellulose extract disposed in the plastic material to seal the pores when it comes into contact with water. A suitable self sealing filter can be obtained from Porex Technologies of Fairburn, Georgia or General Polymeric of West Reading, Pa. This material is an ultra high molecular weight polyethylene having the characteristics described above.

In addition, the self-sealing filters 22, 26 are not limited to the materials described above. Alternatives include a blend of polyethylene beads and cellulose powder that is heated to form a mixture and molded into plugs of the appropriate size. The desired porosity is obtained by controlling the pressure during the molding process, because lower pressure raises the porosity of the resulting plug. Suitable polyethylene beads and cellulose powder can be obtained from bulk chemical suppliers such as Aldrich Chemical Company of Milwaukee, Wisconsin. Another alternate configuration is a stack of alternating layers of a thin (1/16") layer of ultra high molecular weight porous polyethylene and layers of cellulose powder.

The self-sealing filters 22, 26 are normally open, and during normal operation the water trap 10 can be substituted for the water traps disclosed in the above-identified *Ricciardelli* U.S. Pat. No. 4,713,095 or U.S. Pat. No. 4,579,568. However, in the event the collection chamber 16 becomes filled with collected water and water rises in the conduits 24, 28 to come into contact with the self-sealing filters 22, 26, the filters 22, 26 immediately become non-porous, thereby sealing the respective conduits. Because the filters 22, 26 are formed of a porous matrix without large through passageways, the filters 22, 26 provide a barrier to water passage even when in the porous state. When the filters 22, 26 become non-porous, they create an even greater barrier to water passage and they greatly restrict gas flow as well. As explained below, the filters 22, 26 operate as a water sensor which signals undesired water presence to a suitable control system for appropriate action. In this way water and mucous secretions are reliably prevented from entering the gas analyzer. This is an important advantage, because considerable time and expense can be required to clean a gas analyzer once contaminated by liquid.

The water trap 10 can be used in a conventional gas analyzer, in which the physical sealing effect provided by the self-sealing filters 22, 26 protects the gas analyzer from liquid contamination. However, the water trap 10 is preferably used in a gas analyzer which monitors pressure in a conduit coupled to the vacuum port 20 in order to detect sealing by the self-sealing filter 26. FIG. 2 shows a first preferred embodiment of such a gas analyzer 40.

The gas analyzer 40 includes a conventional sample cell 42. Pneumatic conduits 45, 46 interconnect the sample outlet port 18 of the water trap 10 with the sample cell 42 and the sample cell 42 with a primary pump 44 that draws a subatmospheric pressure in the conduits 45, 46. A flow restrictor 47 is interposed in the conduit 46 between the primary pump 44 and the sample cell 42, and a second flow restrictor 49 is interposed between a vent and the pneumatic conduit 46. A pressure sensor PT2 is positioned to monitor pressure in the conduit 46 between the flow restrictor 47 and the sample cell 42.

Another pneumatic conduit 48 interconnects the vacuum port 20 with a secondary pump 50. In addition, a third flow restrictor 56 and a one-way check valve 58 interconnect the conduits 46, 48 as shown. A pressure sensor PT1 develops a pressure signal indicative of pressure in the conduit 48. The two pumps 44, 50 can be considered as constituting a low pressure source.

The sample cell 42 is part of a conventional gas analyzer, which need not be described in greater detail here.

The gas analyzer 40 includes a controller 52 which may, for example, include a programmed microprocessor. This controller 52 receives pressure signals from the pressure sensors PT1, PT2, and it controls operation of the pumps 44, 50. In addition, the controller 52 is provided with a display 54 at which it can indicate an abnormal condition. As explained below, the display 54 can include a visual display with a message such as "Replace Water Trap".

The operation of the controller 52 is illustrated in FIG. 3. As shown in FIG. 3, the controller adjusts the primary pump 44 to obtain a desired flow rate through the conduits 45, 48. In addition, at this point a variable COUNT is set equal to zero. The controller 52 then checks to determine whether COUNT is less than 5, and if so compares the pressure signal developed by the pressure sensor PT2 with a test point TP2. If the pressure measured by the pressure sensor PT2 is greater than TP2, the controller simply loops back to the beginning of the routine flow charted in FIG. 3. TP2 is set at a value below that characteristic of normal operation.

In the event either of the self-sealing filters 22, 26 is sealed or the sample inlet line is clogged (as for example with moisture) the pressure measured by pressure sensor PT2 will be less than TP2. In this event, the controller turns off the primary pump 44 and turns on the secondary pump 50 for ten seconds. The secondary pump 50 draws a higher velocity flow through the conduit 48 and the sample inlet line connected to the port 12 in an attempt to clear the inlet line. Then the controller turns off both pumps 44, 50 for five seconds to allow pressures to stabilize and then compares the pressure measured by the pressure sensor PT1 with a test point TP1. In the event the pressure measured by pressure sensor PT1 is below TP1 (indicating that the self-sealing filter 26 has sealed), the controller 52 turns off both pumps 44, 50 and indicates on the display 54 that the water trap 10 should be replaced. Once the water trap has been replaced, the controller again begins the routine of FIG. 3.

Assuming the pressure measured by the pressure sensor PT1 is greater than TP1, the controller then starts the primary pump 44 at the selected flow rate, increments the variable COUNT and loops as shown in FIG. 3. Because the variable COUNT was originally set equal to 0, this inner loop can be performed a maximum of five times. That is, the controller will attempt to clear the inlet line five times. If after five attempts, the pressure sensed by pressure sensor PT2 remains less than TP2, this is taken as an indication that the sample line is plugged, and the controller turns off both pumps 44, 50 and indicates that the water trap should be replaced as before.

From this discussion, it should be apparent that the gas analyzer 40 monitors the pressure in the conduit 48. In the event this pressure reaches an excessively low value, indicative of a sealed filter 26, the controller turns off the pumps 44, 50 and advises the operator to replace the water trap 10. This approach to recognizing a sealed filter 26 provides many advantages. It is a direct approach, which completely avoids potential problems associated with liquid conductivity, droplet size and liquid sloshing. Furthermore, it can readily be implemented in a reliable electronic system suitable for microprocessor control.

In FIG. 4 is a schematic diagram of a second preferred embodiment of the control system of this invention that it is installed in a gas analyzer 60. The gas analyzer 60 includes a conventional sample cell 62 which receives sample gas from the sample outlet port 18 of the water trap 10. Gas is drawn out of the sample cell 62 via a pneumatic line 64 to a check valve 66 and a normally open valve 68. The normally open valve 68 is connected by an internal filter 70 and a flow restrictor 71 to the inlet of a vacuum pump 72. A normally closed valve 74 is interconnected between a vented $CO_2$ absorber and the pneumatic line 64.

The vacuum port 20 of the water trap 10 is connected by a conduit 78 to an internal filter 80, and via a flow restrictor 82 to the vacuum pump 72.

According to this invention, a pressure sensor PT3 is positioned in the pneumatic line 64 to measure the pressure of the pneumatic line 64 and to provide a pressure signal indicative thereof to a controller 84. In addition, a differential pressure transducer DPT is positioned across the flow restrictor 82 to measure the pressure drop across the flow restrictor 82, and to provide a pressure signal indicative thereof to the controller 84. The controller 84 controls the valves 68, 74 and the pump 72. In addition, the controller 84 controls a display 86 which may be of the type described above. In operation, the valve 68 is normally open and the valve 74 is normally closed. A sample is drawn through the sample cell 62 by the pump 72, and water is drawn out of the separation chamber 14 by an air flow through collection chamber 16, the conduit 78 to the pump 72.

The differential pressure transducer DPT is used to monitor flow through the conduit 78. With a normal flow through the conduit 78 there will be a perceptible pressure drop across the restrictor 82. However, if the pump 72 is operating normally and the pressure drop across the restrictor 82 measured by the differential pressure transducer DPT goes to zero, the controller takes this as a signal that the self-sealing filter 26 has sealed. In this event, the controller 84 turns off the pump 72 and displays an appropriate message on the display 86.

In the event the pressure transducer PT3 indicates an excessively low pressure (characteristic of a clogged inlet line), the controller 84 closes the valve 68 and opens the valve 74 to reverse the flow through the sample cell 62. If desired, the pump 72 can be run at higher speed to increase the flow rate through the inlet line in order better to clear any obstruction.

Of course, it should be understood that a wide range of changes and modifications can be made to the preferred embodiments described above. For example, the self-sealing filters described above can be used with a wide variety of water traps for respiration gas analyzers. Furthermore, the water trap of this invention can be used with a wide variety of gas analyzers, including gas analyzers which do not include the improved control system described above. The control system of this invention can be implemented in programmed microprocessors or in analog circuitry, and the widest variety of pressure sensors can be used.

It is therefore intended that the foregoing detailed description be regarded as illustrative rather than limiting, and that it be understood that it is the following claims, including all equivalents, which are intended to define the scope of this invention.

We claim:
1. A water trap for a respiration gas analyzer, said water trap comprising:
   a tapered water separation chamber;
   a sample inlet port connected to the water separation chamber;
   a sample outlet port connected to the water separation chamber by a sample outlet conduit;
   a water collection chamber connected to the water separation chamber;
   a vacuum port connected to the water collection chamber by a vacuum conduit; and
   at least one self-sealing filter disposed in at least one of the sample outlet conduit and the vacuum conduit, said self-sealing filter comprising a porous matrix having pores characterized by a pore size less than about 100 microns and means, disposed in the porous matrix, for rendering the porous matrix substantially non-porous when exposed to water, said pores forming the only flow path through the filter.

2. The invention of claim 1 wherein the porous matrix comprises an ultra high molecular weight polyethylene.

3. The invention of claim 1 wherein the pore size is in the range of about 15–35 microns.

4. The invention of claim 1 wherein the means for rendering the porous matrix substantially non-porous comprises cellulose.

5. The invention of claim 1 wherein the at least one self-sealing filter comprises two self-sealing filters, each positioned in a respective one of the conduits.

6. The invention of claim 5 wherein the chambers, ports, and conduits are molded in a modular assembly which can be handled as a single unit once assembled.

7. In a gas analyzer of the type comprising a sample cell, a water trap comprising a separation chamber interconnected with a water collection chamber, a low pressure source, and a conduit system comprising a first conduit for conducting a sample gas from an inlet line to the separation chamber, a second conduit for conducting the sample gas from the separation chamber, through the sample cell to the low pressure source, and a third conduit for conducting a gas from the water collection chamber to the low pressure source, the improvement comprising;

means, included in the third conduit, for automatically sealing the third conduit upon contact with water;

a pressure sensor coupled to the third conduit to generate a pressure signal indicative of a pressure parameter of a selected portion of the third conduit;

means, responsive to the pressure signal, for detecting when the pressure signal is indicative of an abnormally low flow through the third conduit; and means, responsive to the detecting means, for indicating an abnormal condition when the detecting means detects the abnormally low flow;

said sealing means comprising a self-sealing filter comprising a porous matrix having pores characterized by a pore size less than about 100 microns and means, disposed in the porous matrix, for rendering the porous matrix substantially non-porous when exposed to water, said pores forming the only flow path through the filter.

8. The invention of claim 7 wherein the pressure sensor is indicative of a pressure drop across a selected segment of the third conduit and therefore of flow through the selected segment.

9. The invention of claim 7 wherein the pressure sensor is indicative of pressure within the selected portion of the third conduit.

10. The invention of claim 7 wherein the indicating means comprises means for displaying an abnormal condition signal when the detecting means detects the abnormally low flow.

11. The invention of claim 7 wherein the indicating means comprises means for interrupting operation of the low pressure source.

12. The invention of claim 7 wherein the low pressure source comprises a plurality of pumps.

13. The invention of claim 7 wherein the sealing means is disposed in the water trap.

14. The invention of claim 7 wherein the porous matrix comprises an ultra high molecular weight polyethylene.

15. The invention of claim 14 wherein the pore size is in the range of about 15–35 microns.

16. The invention of claim 15 wherein the means for rendering the porous matrix substantially non-porous comprises cellulose.

* * * * *